US00PP36096P2

(12) United States Plant Patent
Heuger

(10) Patent No.: US PP36,096 P2
(45) Date of Patent: Sep. 3, 2024

(54) ***HELLEBORUS* PLANT NAMED 'HL 1022'**

(50) Latin Name: ***Helleborus niger* X *Helleborus* x *hybridus***
Varietal Denomination: HL 1022

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 18/518,883

(22) Filed: Nov. 24, 2023

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Helleborus* plant named 'HL 1022' characterized by its upright to somewhat outwardly spreading and mounded plant habit; moderately vigorous growth habit; dark green-colored leaflets with lighter green-colored venation; freely flowering habit; purplish red-colored flowers; and good garden performance.

2 Drawing Sheets

Figure 1:
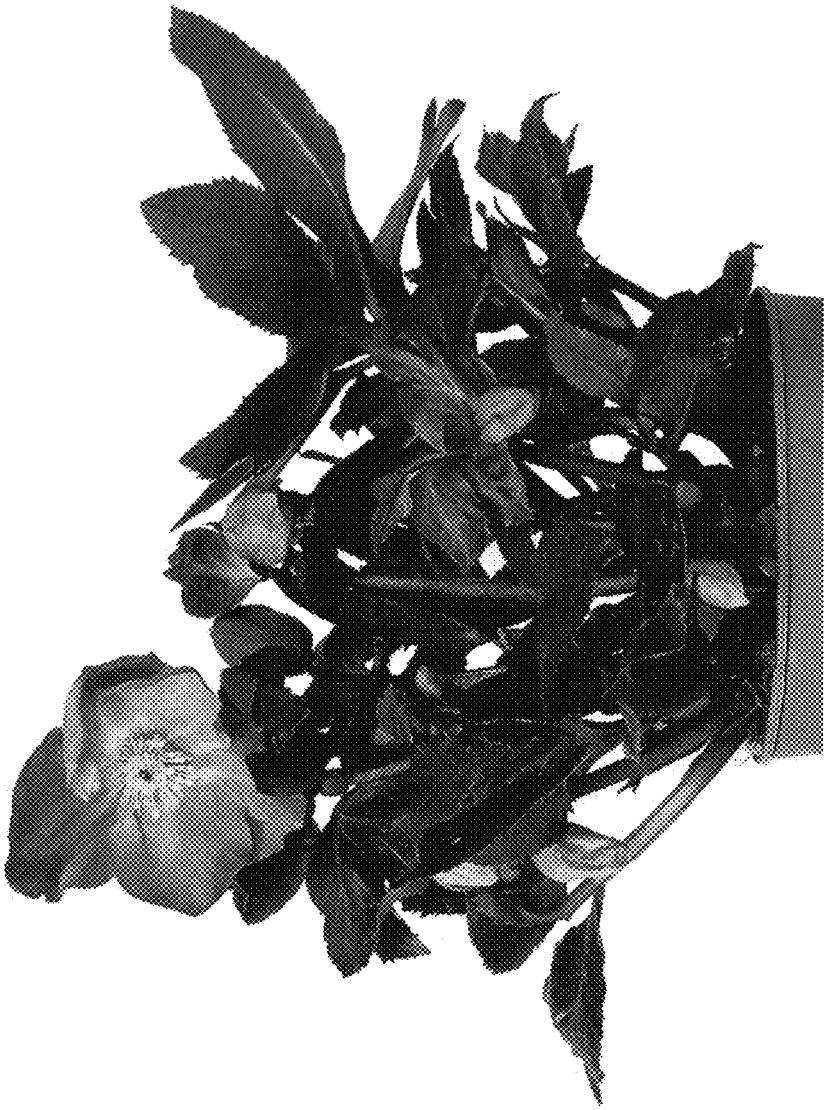

Botanical designation: *Helleborus niger* X *Helleborus* x *hybridus*.

Cultivar denomination: 'HL 1022'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Dec. 1, 2022, application number 2022/2752. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus niger* X *Helleborus* x *hybridus* and hereinafter referred to by the name 'HL 1022'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stresses.

The new *Helleborus* plant originated from a cross-pollination conducted by the Inventor in Glandorf, Germany in November, 2015 of a proprietary selection of *Helleborus niger* identified as code number P881, not patented, as the female, or seed, parent and a proprietary selection of *Helleborus* x *hybridus* identified as code number O1446, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in December, 2017.

Asexual reproduction of the new *Helleborus* plant by in vitro axillary meristem culture in a controlled environment in Glandorf, Germany since April, 2018 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HL 1022'. These characteristics in combination distinguish 'HL 1022' as a new and distinct *Helleborus* plant:

1. Upright to somewhat outwardly spreading and mounded plant habit.
2. Moderately vigorous growth habit.
3. Dark green-colored leaflets with lighter green-colored venation.
4. Freely flowering habit.
5. Purplish red-colored flowers.
6. Good garden performance.

Plants of the new *Helleborus* differ from plants of the female parent selection in the following characteristics:

1. Leaflets of plants of the new *Helleborus* are darker green in color than leaflets of plants of the female parent selection.

2. Flowers of plants of the new *Helleborus* are darker purplish red in color than flowers of plants of the female parent selection.

Plants of the new *Helleborus* differ from plants of the male parent selection in the following characteristics:

1. Leaflets of plants of the new *Helleborus* are darker green in color than leaflets of plants of the male parent selection.
2. Flowers of plants of the new *Helleborus* are lighter purplish red in color than flowers of plants of the male parent selection.

Plants of the new *Helleborus* can also be compared to plants of *Helleborus niger* 'COSEH 1010', disclosed in U.S. Plant Pat. No. 25,314. In side-by-side comparisons, plants of the new *Helleborus* differ primarily from plants of 'COSEH 1010' in the following characteristics:

1. Plants of the new *Helleborus* have larger leaves than plants of 'COSEH 1010'.
2. Plants of the new *Helleborus* have larger flowers than plants of 'COSEH 1010'.
3. Flowers of plants of the new *Helleborus* are purplish red in color whereas flowers of plants of 'COSEH 1010' are white in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'HL 1022' grown in a container.

Figure 2:
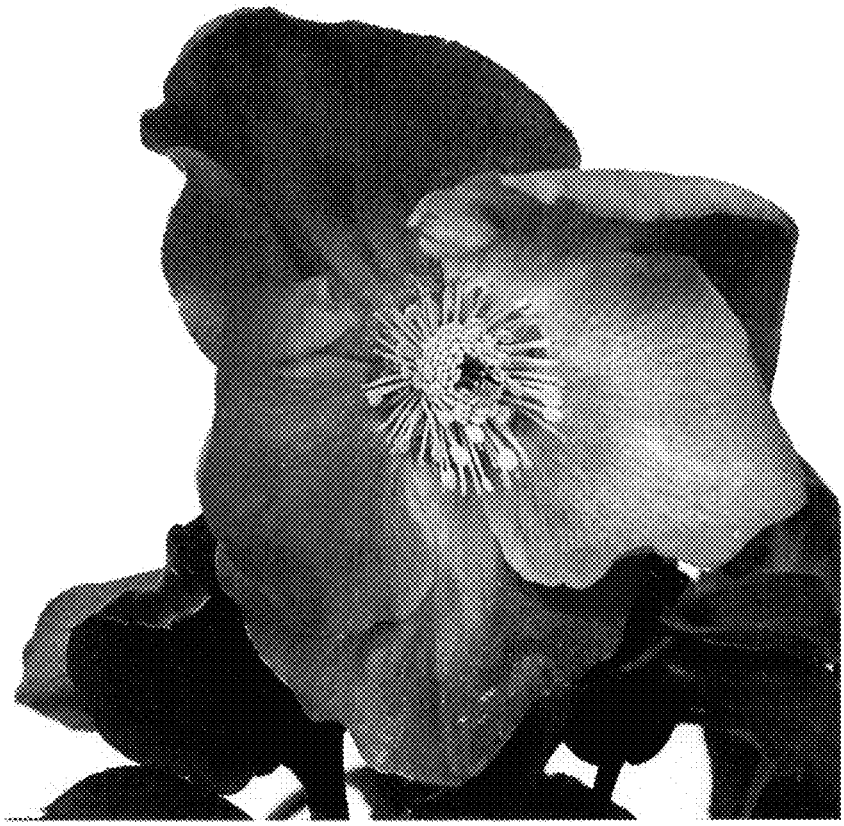

The photograph on the second sheet (FIG. 2) is a close-up view of a typical flower and flower bud of 'HL 1022'.

DETAILED BOTANICAL DESCRIPTION

The aforementioned photographs and following observations, measurements and values describe plants grown during the late autumn in 17-cm containers in a glass-covered greenhouse in Glandorf, Germany and under cultural practices typical of commercial *Helleborus* production. During the production of the plants, day temperatures ranged from 12C to 32C and night temperatures ranged from 5C to 12C. Plants were 48 weeks old when the photographs were taken and 14 months old when the description was taken. In the following description, color references are made to The Royal Horticultural Society Colour Chart, 2015 Edition, except where general terms of ordinary dictionary significance are used.

Botanical classification: *Helleborus niger* X *Helleborus* x *hybridus* 'HL 1022'.

Parentage:

*Female, or seed, parent.*—Proprietary selection of *Helleborus niger* identified as code number P881, not patented.

*Male, or pollen, parent.*—Proprietary selection of *Helleborus* x *hybridus* identified as code number O1446, not patented.

Propagation:

*Type.*—In vitro axillary meristem culture.

*Time to initiate roots, winter.*—About 55 days at temperatures about 12C.

*Time to produce a rooted young plant, winter.*—About 170 days at temperatures ranging from about 4C to 15C.

*Root description.*—Thick to thin, fleshy; typically white to brownish in color, actual color of the roots is dependent on substrate composition, water quality, fertilizer type and formulation, substrate temperature and physiological age of roots.

*Rooting habit.*—Low branching; sparse.

Plant description:

*Plant and growth habit.*—Herbaceous perennial; upright to somewhat outwardly spreading and mounding plant habit with flowers held with and slightly above the foliar plane; plant shape, flattened globular; moderately vigorous growth habit and moderate to slow growth rate.

*Plant height, soil level to top of foliar plane.*—About 21.8 cm.

*Plant height, soil level to top of flowers.*—About 25.4 cm.

*Plant diameter* (*area of spread*).—About 43 cm.

Leaf description:

*Arrangement.*—Leaves arranged in a basal rosette; leaves palmately compound with typically five, or occasionally, seven, leaflets per leaf.

*Leaf length.*—About 18.9 cm.

*Leaf width.*—About 22.7 cm.

*Leaflet length.*—About 12.7 cm.

*Leaflet width.*—About 6.5 cm.

*Leaf shape.*—Palmate; roughly reniform in outline.

*Leaflet shape.*—Ovate to elliptic.

*Leaflet apex.*—Acute.

*Leaflet base.*—Attenuate.

*Leaflet margin.*—Serrate; slightly coarsely undulate.

*Leaflet texture and luster, upper and lower surfaces.*—Smooth, glabrous; coriaceous and tough; moderately glossy.

*Leaflet venation pattern.*—Pinnate and reticulate.

*Leaflet color.*—Developing leaflets, upper surface: Close to 137B; at the base, close to 187A. Developing leaflets, lower surface: Close to 147B; midvein, close to 187A. Fully developed leaflets, upper surface: Darker than a blend of NN137A and 147A; at the base, slightly tinged with close to 200B and 200C; venation, close to 146C. Fully developed leaflets, lower surface: Close to 147B; venation, close to 146C.

*Petioles.*—Length: About 14.8 cm. Diameter: About 7 mm by 8 mm. Strength: Strong. Texture and luster, upper and lower surfaces: Smooth, glabrous; slightly glossy. Color, upper and lower surfaces: Close to 146B; moderately to heavily covered with fine dots, close to 200A and 200B.

Flower description:

*Flower shape and habit.*—Single rotate bowl-shaped flowers arranged in panicles; freely flowering habit with about two to five flowers per inflorescence and about 24 flowers and flower buds per plant; flowers face mostly outwardly to slightly nodding.

*Fragrance.*—None detected.

*Natural flowering season.*—Plants begin flowering about ten months after planting; plants flower naturally from late autumn into the winter in Germany.

*Flower longevity on the plant.*—About ten days; sepals persistent, other flower parts are not persistent.

*Flower buds.*—Length: About 3.7 cm. Diameter: About 1.6 cm. Shape: Narrowly ovate to oblong. Texture and luster: Smooth, glabrous; matte. Color: Close to 182B; towards the margins, tinged with close to 187B; towards the base, close 145C to 145D.

*Inflorescence height (including peduncle).*—About 23.8 cm.

*Inflorescence diameter.*—About 14.7 cm.

*Flower diameter.*—About 10.3 cm.

*Flower depth.*—About 5.7 cm.

*Petals.*—All petals are transformed into nectaries.

*Sepals.*—Quantity and arrangement: About five, occasionally, six, arranged in a single whorl. Length: About 6.4 cm. Width: About 6.2 cm. Shape: Broadly ovate to close to orbicular; moderately concave. Apex: Broadly and bluntly acute to obtuse. Base: Cuneate. Margin: Entire; coarsely undulate. Texture and luster, upper surface: Smooth, glabrous; matte. Texture and luster, lower surface: Smooth, glabrous; matte to slightly glossy. Color: When opening, upper surface: Close to a blend of 155B and 186A to 186C. When opening, lower surface: Close to a blend of 157D and 186A to 186C; venation, close to N186D. Fully opened, upper surface: Close to 186A to 186C and finely flushed with close to 75C; distally, tinged with close to 147A; at the base, close to 145B; venation, similar to lamina colors; color does not change with subsequent development. Fully opened, lower surface: Close to 186A to 186D; distally, close to 147A; venation, close to N186C; color does not change with subsequent development.

*Flower bracts.*—Quantity per flower: Typically one. Length: About 8.8 cm. Width: About 6 cm. Shape: Ovate to obovate. Apex: Acute to three-lobed. Base: Truncate to broadly cuneate. Margin: Mostly entire; distally, serrate; coarsely undulate. Color, upper surface: Close to a blend of NN137A and 147A; towards the base, close to 145A to 145B. Color, lower surface: Close to 147B; midvein, close to N186C and distally, close to 183A.

*Peduncles.*—Length: About 16.9 cm. Diameter: About 1 cm to 1.1 cm. Aspect: About 10 degrees from vertical. Strength: Strong. Texture and luster: Smooth, glabrous; slightly to moderately glossy. Color: Close to 144A to 144B; moderately to heavily covered with fine dots, close to N186C.

*Pedicels.*—Length: About 4.8 cm. Diameter: About 4 mm. Aspect: About 30 degrees from peduncle axis. Strength: Moderately strong. Texture and luster: Smooth, glabrous; moderately glossy. Color: Close to 146B to 146C; heavily covered with fine dots, close to N186C.

*Reproductive organs.*—Stamens: Quantity per flower: About 120. Filament length: About 1.9 cm. Filament color: Close to 155A. Anther shape: Double and broadly reniform; basifixed. Anther size: About 2.5 mm by 3 mm. Anther color: Close to 154C. Pollen amount: Sparse to moderate. Pollen color: Close to 4D to lighter than 4D. Pistils: Quantity per flower: About five to eight. Pistil length: About 1.2 cm. Stigma diameter: About 0.3 mm. Stigma shape: Club-shaped. Stigma color: Close to 157A. Style length: About 1.15 cm. Style color: Close to 187B. Ovary color: Close to 150C. Nectaries (transformed petals): Quantity per flower: About 18. Length: About 1.4 cm. Diameter: About 6 mm. Shape: Tubular, flattened; apices, obtuse. Texture and luster, inner and outer surfaces: Smooth, glabrous; slightly glossy. Color, immature, inner and outer surfaces: Close to 144C; at the base, close to 144B. Color, mature, inner and outer surfaces: Close to N144C; towards the apex, close to 151A and 151B; at the base, close to 151A; venation, similar to lamina colors; with subsequent development, color becoming closer to N144A, towards the apex, closer to 151A, at the apex, closer to 172A to 172B and at the base, closer to 152D. Seeds and fruits: To date, seed and fruit development have not been observed on plants of the new *Helleborus*.

Garden performance: Plants of the new *Helleborus* have been observed to have good garden performance and to tolerate rain, wind, high temperatures about 35C and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HL 1022' as illustrated and described.

* * * * *